(12) United States Patent
Vazquez

(10) Patent No.: US 9,943,223 B2
(45) Date of Patent: Apr. 17, 2018

(54) RETINAL NERVE FIBER LAYER VOLUME ANALYSIS FOR DETECTION AND PROGRESSION ANALYSIS OF GLAUCOMA

(71) Applicant: UNIVERSITY OF MIAMI, Miami, FL (US)

(72) Inventor: Luis E. Vazquez, Coral Gables, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 61 days.

(21) Appl. No.: 15/041,508

(22) Filed: Feb. 11, 2016

(65) Prior Publication Data
US 2016/0235289 A1 Aug. 18, 2016

Related U.S. Application Data

(60) Provisional application No. 62/116,195, filed on Feb. 13, 2015.

(51) Int. Cl.
| | |
|---|---|
| *A61B 3/00* | (2006.01) |
| *G06T 7/00* | (2017.01) |
| *A61B 3/10* | (2006.01) |
| *G06T 7/11* | (2017.01) |
| *G06T 7/62* | (2017.01) |

(52) U.S. Cl.
CPC ............ *A61B 3/0025* (2013.01); *A61B 3/102* (2013.01); *G06T 7/0014* (2013.01); *G06T 7/11* (2017.01); *G06T 7/62* (2017.01); *G06T 2207/10101* (2013.01); *G06T 2207/30041* (2013.01)

(58) Field of Classification Search
CPC ....... G06T 7/0012; G06T 7/0014; G06T 7/11; G06T 7/136; G06T 7/62; G06T 2207/10101; G06T 2207/30041; A61B 3/0025; A61B 3/102; A61B 3/12
See application file for complete search history.

(56) References Cited

U.S. PATENT DOCUMENTS

| | | | |
|---|---|---|---|
| 8,474,978 B2 | 7/2013 | Huang et al. | A61B 3/102 |
| 8,801,187 B1 | 8/2014 | Knighton et al. | A61B 3/102 |
| 8,840,248 B2 | 9/2014 | Imamura | G06T 7/0012 |
| 2003/0114740 A1* | 6/2003 | Essock et al. | 600/407 |
| 2008/0312552 A1* | 12/2008 | Zhou et al. | 600/558 |
| 2009/0073387 A1* | 3/2009 | Meyer et al. | 351/246 |
| 2011/0137157 A1* | 6/2011 | Imamura et al. | 600/425 |

* cited by examiner

*Primary Examiner* — Andrew W Johns
(74) *Attorney, Agent, or Firm* — Marshall, Gerstein & Borun LLP

(57) ABSTRACT

Methods and systems of analyzing retinal nerve fiber layer for detecting glaucoma and/or other retinal nerve fiber indicated eye conditions include collecting retinal nerve fiber layer image data, segmenting the retinal nerve fiber layer image data by removing retinal nerve fiber layer image data below a threshold thickness value, determining an area or a volume of the thickness of the retinal nerve fiber layer in the retinal region of interest; and determining a severity of the glaucoma and/or at least one other retinal nerve fiber indicated eye condition for the subject.

20 Claims, 7 Drawing Sheets
(4 of 7 Drawing Sheet(s) Filed in Color)

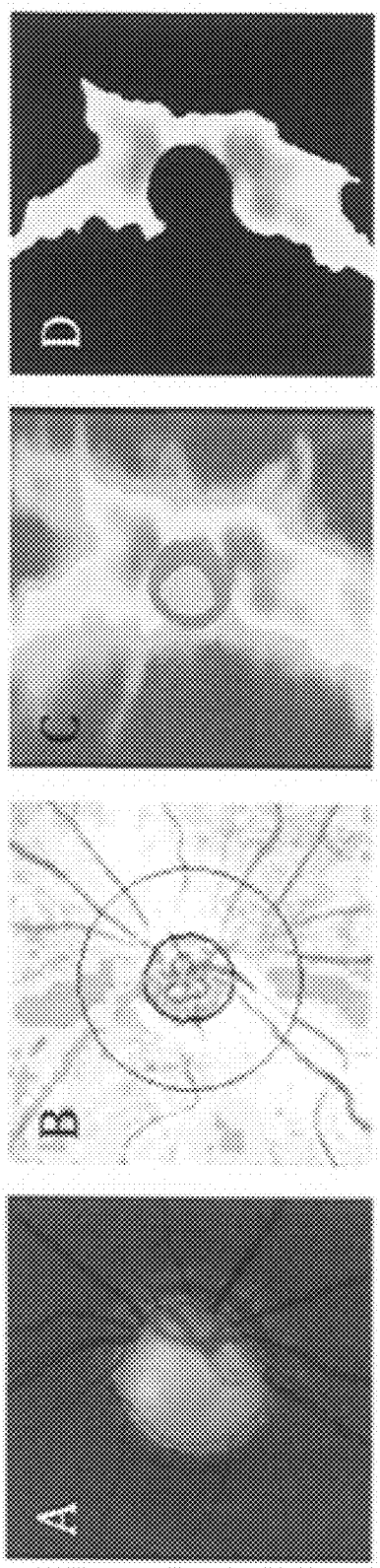

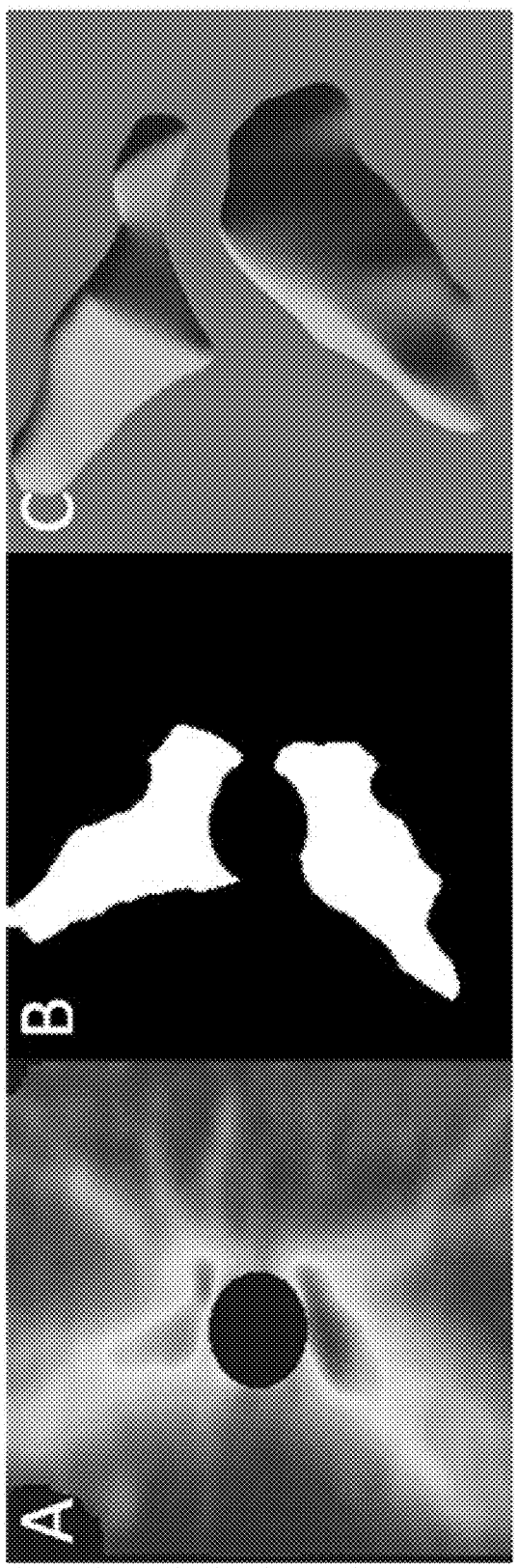

| GCIPL Parameter | AUC | rNFL Parameter | AUC | rNFL Bundle Parameter | AUC |
|---|---|---|---|---|---|
| Minimum | 0.959 | Average | 0.939 | Sum of Superior and Inferior Bundle Volume | 0.970 |
| Average | 0.935 | | | | |
| Superior | 0.875 | Superior | 0.936 | Superior Bundle Area | 0.927 |
| Superotemporal | 0.919 | | | Superior Bundle Volume | 0.934 |
| Superonasal | 0.816 | | | | |
| Inferior | 0.918 | Inferior | 0.933 | Inferior Bundle Area | 0.970 |
| Inferotemporal | 0.956 | | | Inferior Bundle Volume | 0.970 |
| Inferonasal | 0.835 | | | | |

| Parameter | Mean (SD) | | | One-Way ANOVA P |
|---|---|---|---|---|
| | Mild | Moderate | Severe | |
| HVF MD | -2.90 (1.50) | -8.84 (1.22) | -18.01 (4.52) | <0.0001 |
| Sum Area (mm2) | 2.34 (1.53) | 1.71 (1.51) | 0.40 (0.36) | 0.0003 |
| Superior Area (mm2) | 1.39 (0.86) | 1.03 (0.78) | 0.23 (0.29) | <0.0001 |
| Inferior Area (mm2) | 0.95 (0.82) | 0.68 (1.04) | 0.17 (0.26) | 0.0144 |
| Sum Volume (Vmm3) | 300.8 (207.1) | 214.4 (199.0) | 47.3 (42.8) | 0.0004 |
| Superior Volume (Vmm3) | 176.6 (115.3) | 127.9 (99.8) | 27.4 (35.9) | 0.0001 |
| Inferior Volume (Vmm3) | 124.2 (112.0) | 86.5 (139.3) | 19.9 (29.6) | 0.0159 |
| Average rNFL (um) | 66.9 (9.8) | 61.6 (9.5) | 55.2 (6.4) | 0.0012 |
| Superior rNFL (um) | 82.6 (16.0) | 76.8 (17.0) | 61.5 (9.7) | 0.0004 |
| Inferior rNFL (um) | 76.5 (18.2) | 66.6 (16.3) | 58.8 (8.7) | 0.0052 |
| Minimum GCIPL (um) | 58.0 (8.7) | 52.9 (10.2) | 50.6 (6.8) | 0.0311 |

FIG. 6

RETINAL NERVE FIBER LAYER VOLUME ANALYSIS FOR DETECTION AND PROGRESSION ANALYSIS OF GLAUCOMA

CROSS-REFERENCE TO RELATED APPLICATIONS

This application claims the benefit of U.S. Provisional Application Ser. No. 62/116,195, filed Feb. 13, 2015, entitled "Retinal Nerve Fiber Layer Volume Analysis For Detection And Progression Analysis Of Glaucoma" the entirety of which is hereby incorporated herein by reference.

The present disclosure relates to glaucoma and other eye-related diseases detection

FIELD OF THE INVENTION

The present disclosure relates to glaucoma and other eye-related diseases detection and, more specifically, for detecting glaucoma and eye disease using retinal nerve fiber layer analysis.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Glaucoma is a neurodegenerative disease of the optic nerve leading to irreversible blindness. In simple terms, it is defined by loss of nerve fibers in the optic nerve, diagnosed by observation of neuroretinal rim loss in the optic nerve head (ONH) (FIG. 1A). Early detection and treatment of glaucoma can slow down the disease progression and prevent significant visual impairment. Detection of early glaucoma is best achieved by evaluating the retinal nerve fiber layer (rNFL) by optical coherence tomography (OCT). OCT analysis of the rNFL in essence measures the thickness of the nerve bundles that make up the optic nerve prior to entering the optic nerve, while emerging from the retina. The current measurement is made by evaluating the thickness of the rNFL 3.6 mm around the center of the optic nerve head (ONH) (as shown in a circle in FIG. 1B). However, the rNFL around the optic nerve head is complex, and measurement of the area 3.6 mm from the center of the ONH is merely a sample of the nerve bundles.

There are other eye diseases, in addition to glaucoma, that affect the nerve fiber bundles, including optic neuropathy, papilledema, optic neuritis and multiple sclerosis (MS), and idiopathic intracranial hypertension (IIH). It is desirable to have more accurate techniques for measuring each of these conditions, as well as others related to changes in never fiber bundle.

SUMMARY OF THE INVENTION

The present application describes techniques for detection of the onset and/or progression of glaucoma and other eye diseases by analyzing the area and/or volume of (superior and inferior) retinal nerve fiber layers. The other eye-related conditions include optic neuropathy, multiple sclerosis (MS) with optical neuritis, papilledema, idiopathic intracranial hypertension (IIH), etc.

In accordance with an example, a method of analyzing retinal nerve fiber layer for detecting glaucoma and/or other retinal nerve fiber indicated eye conditions in a subject, the method comprises: collecting, using a glaucoma analysis processing device, retinal nerve fiber layer image data, the image data containing fiber layer thickness data for a region of interest of the retinal nerve fiber layer image data; segmenting, using a glaucoma analysis processing device, the retinal nerve fiber layer image data by removing retinal nerve fiber layer image data below a threshold thickness value over the region of interest, wherein segmenting the retinal nerve fiber layer image data segments a retinal region of interest; determining, using a glaucoma analysis processing device and from the segmented retinal nerve fiber layer image data, an area or a volume of the thickness of the retinal nerve fiber layer in the retinal region of interest; and determining, using a glaucoma analysis processing device and from the area or the volume, a severity of the glaucoma and/or at least one other of the other retinal nerve fiber indicated eye conditions for the subject.

In accordance with another example, a system comprises: one or more processors and one or more memories, the one or more memories storing instructions that when executed by the one or more processors, cause the one or more processors to; collect, retinal nerve fiber layer image data, the image data containing fiber layer thickness data for a region of interest of the retinal nerve fiber layer image data; segment the retinal nerve fiber layer image data by removing retinal nerve fiber layer image data below a threshold thickness value over the region of interest, wherein segmenting the retinal nerve fiber layer image data segments out a retinal thickness data region of interest; determine, from the segmented retinal nerve fiber layer image data, an area or a volume of the desired retinal thickness data region of interest; and determine, from the area or the volume, a severity of glaucoma and/or at least one other retinal nerve fiber indicated eye condition for the subject.

Diseases here include comparative optic neuropathy, toxic/metabolic optic neuropathy, ischanic optic neuropathy, inherited optic neuropathy, IIH, MS, papilledema, and others.

In accordance with another example, an apparatus for analyzing retinal nerve fiber layers for detecting glaucoma and/or other retinal nerve fiber indicated eye conditions in a subject, the apparatus comprises: one or more processors and one or more memories, the one or more memories storing; a collecting module configured to collect, retinal nerve fiber layer image data, the image data containing fiber layer thickness data for a region of interest of the retinal nerve fiber layer image data; a segmenting module configured to segment the retinal nerve fiber layer image data by removing retinal nerve fiber layer image data below a threshold thickness value over the region of interest, wherein segmenting the retinal nerve fiber layer image data segments out a superior retinal thickness data region and an inferior retinal thickness data region; a determining module configured to determine, from the segmented retinal nerve fiber layer image data, an area or a volume of the superior retinal nerve fiber layer thickness data region and the inferior retinal nerve fiber layer thickness data region; and a diagnostic module configured to determine, from the area or the volume, a severity of glaucoma and/or at least one other retinal nerve fiber indicated eye condition for the subject.

BRIEF DESCRIPTION OF THE DRAWINGS

This patent or application file contains at least one drawing executed in color. Copies of this patent or patent application publication with color drawing(s) will be provided by the United States Patent and Trademark Office upon request and payment of the necessary fee.

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 1A illustrates an image of the optic nerve head showing loss of nerve fibers in the optic nerve, diagnosed by observation of neuroretinal rim loss. FIG. 1B illustrates a current measurement technique for the optic nerve head, one that evaluates the thickness of the retinal nerve fiber layer (rNFL).

FIG. 1C illustrates a retinal image obtained with spectrum domain optical coherence tomography (SD-OCT) technique, segmented to isolate the nerve fiber layer, which results in a peripapillary rNFL thickness map.

FIG. 1D illustrates the image data of FIG. 1C after performing threshold analysis of the thickness map to obtain the area of the thicker superior and inferior nerve bundles.

FIGS. 2A-2C illustrate imaging processing steps that may be implemented by a glaucoma analysis processing machine to select nerve fiber layer bundles determine presence and/or progression of glaucoma. FIG. 2A is plot of retinal nerve fiber layer image data for an optical tomography coherence (OCT) image data of the retinal nerve bundles. FIG. 2B illustrates image data of FIG. 2A after a threshold mask has been applied. FIG. 2C is a resulting area or volume map determined from the image data of FIG. 2B.

FIG. 6 is table of empirical data obtained for mild, moderate, and sever glaucoma, as determined from measuring either the total area of image data, e.g., image data in FIG. 3C, or the total volume of image data, e.g., image data in FIG. 4C.

DETAILED DESCRIPTION

Figure 3A:
FIG. 3A illustrates examples of segmented superior and inferior image data for a plurality of subjects having a normal eye function, that is, not exhibiting glaucoma or glaucoma onset, in accordance with an example.

This patent or application file contains at least one drawing executed in color. Copies of this patent or patent application publication with color drawing(s) will be provided by the United States Patent and Trademark Office upon request and payment of the necessary fee.

The nerve bundles superior and inferior of the ONH are the thickest, and the first ones to suffer glaucomatous damage. Their thickness gives the impression of butterfly wings around the ONH in a thickness map of the peripapillary rNFL. The present application proposes a different analysis tool for current spectral domain OCT (SD-OCT) images for detection of glaucoma by measuring the volume of the superior and inferior nerve bundles around the ONH. Retinal images obtained with SD-OCT are segmented to isolate the nerve fiber layer, which results in a peripapillary rNFL thickness map (FIG. 1C). The novel component starts with performing threshold analysis of the thickness map to obtain the area of the thicker superior and inferior nerve bundles (FIG. 1D). The thickness values are incorporated to obtain the volume. This volume is compared to a normative database to detect differences from the normal. Thinner volumes (compared to normative data) are indicative of glaucoma or other eye diseases, such as optic neuropathy (from various etiologies including inherited, metabolic, toxic, compressive, and ischemic), and thicker volumes can represent papilledema or other eye diseases, such as IIH and MS. An individual's superior and inferior nerve bundle thickness can be compared over time to assess disease progression. In addition, the thickness or volume of the regions of the image outside of the superior and inferior bundles may be used for the other eye-related diseases stated above.

FIGS. 2A-2C illustrates imaging processing steps that may be implemented by a glaucoma analysis processing machine to select nerve fiber layer bundles determine presence and/or progression of glaucoma. FIG. 2A is plot of retinal nerve fiber layer image data collected from an imaging machine. The image data in this example is optical tomography coherence (OCT) image data of the retinal nerve bundles. The OCT image data is an example of image data that represents the thickness of the retinal nerve bundles, wherein the illustrated example, the intensity of image data correlates to the thickness of the nerve bundles.

FIG. 2B illustrates a threshold mask that may be applied to the collected retinal nerve image data, as a part of a segmenting of that image data. The threshold may be an intensity threshold or a corresponding intensity threshold. The threshold may be predetermined from historical patient data, such as from a general patient population or patient population corresponding to a population demographic specifically identified based on the subject. In other examples, the threshold may be determined based on historical retinal image data for the subject specifically, such as past glaucoma tests. In yet other examples, the threshold may be determined from the collected image data from FIG. 2A. In other words, one or many threshold values can be applied to an OCT image to select the desired rNFL bundle. Measurements of the size or volume of the selected rNFL bundle has diagnostic value.

In detecting the presence or progression of glaucoma or other eye diseases, the image data of FIG. 2A is segmented using the threshold value of FIG. 2B to remove image data below the threshold. From the resulting image data, an area or volume map is determined and plotted in FIG. 2C.

The generated image data in FIG. 2C is characterized by an inner retinal ring region corresponding to the subject's optic nerve. This inner ring region contains no image data, generally speaking. The generated image data further includes, as a result of the segmentation, a superior retinal thickness data region, positioned superior to the optic nerve, and an inferior retinal thickness data region, positioned inferior to the optic nerve. From one or both of these superior and inferior retinal thickness data regions, glaucoma and/or the progression of glaucoma can be detected, specifically from looking at the total area covered by the segmented image data or from the total volume of the segmented image data.

FIG. 3A illustrates examples of the area of segmented superior and inferior image data for a plurality of subjects having a normal eye function, that is, not exhibiting glaucoma or glaucoma onset. The segmented image data reflects a large area in the both the superior retinal region and the inferior retinal region.

Figure 3B:
FIG. 3B illustrates examples of segmented superior and inferior image data for a plurality of subjects exhibiting various stages of glaucoma, in accordance with an example.

FIG. 3B illustrates examples of the area of segmented superior and inferior image data for a plurality of subjects exhibiting various stages of glaucoma. The segmented image data reflects a greatly reduced area in the both the superior retinal region and the inferior retinal region.

Figure 3C:
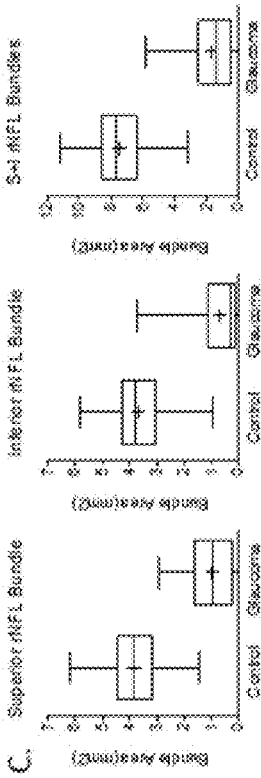
FIG. 3C illustrates a comparison of the total area of superior retinal region for the control subjects (having no glaucoma) and those subjects exhibiting glaucoma, in accordance with an example.

FIG. 3C illustrates a comparison of the total area of superior retinal region for the control subjects (having no glaucoma) and those subjects exhibiting glaucoma. Similar data is plotted for the total area for the inferior retinal region, and for the combined area of the superior and inferior retinal image data. The corresponding total area values are shown as well. The data indicates a substantial reduction in total area over the segmented regions for subjects that have glaucoma.

Figure 4A:
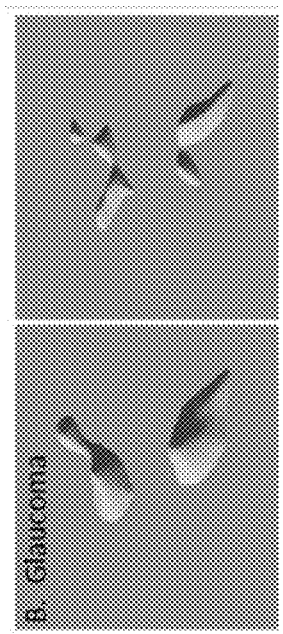
FIGS. 4A and 4B illustrate similar image data to that of FIGS. 3A and 3B, correspondingly, but showing total volume instead of total area.
Figure 4B:
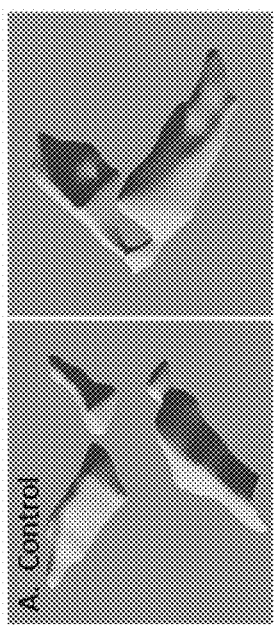
Figure 4C:
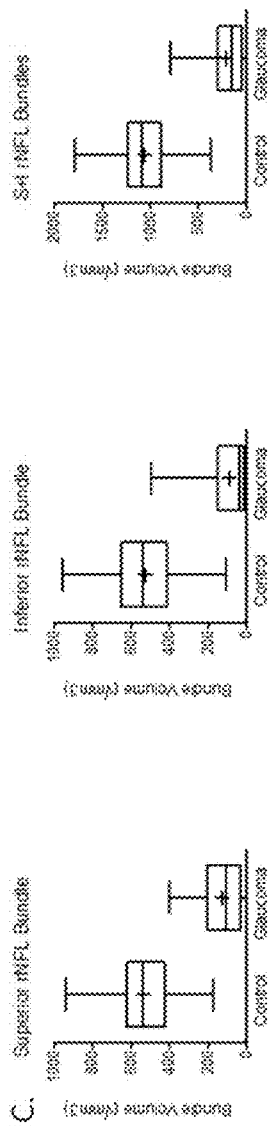
FIG. 4C provides data of the total volume for the super retinal rNFL bundle region and the inferior retinal rNFL bundle region.

FIGS. 4A and 4B illustrate similar image data to that of FIGS. 3A and 3B. Whereas the total image of the segmented image data was analyzed to determine a severity of glaucoma for FIG. 3C, for FIG. 4C the glaucoma analysis device has determined the total volume for the super retinal rNFL bundle region and the inferior retinal rNFL bundle region. As illustrated, subjects experiencing glaucoma have considerably reduced total retinal nerve layer volume in the superior and inferior regions.

Figure 5:
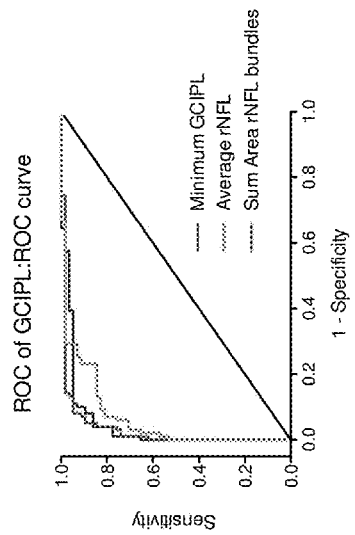
FIG. 5 plots a comparison of the effectiveness of examples herein against a conventional ganglion cell-inner plexiform layer (GCIPL) glaucoma test and a retinal nerve fiber layer rNFL thickness test.

FIG. 5 plots a comparison of the effectiveness of the present techniques, in an example empirical testing, against a conventional ganglion cell-inner plexiform layer (GCIPL) glaucoma test and a retinal nerve fiber layer rNFL thickness test.

The present techniques are not only able to detect the presence of glaucoma, but unlike conventional techniques, they are able to identify the severity of glaucoma. For example, as illustrated by the empirical data obtained and provided in FIG. 6, the present techniques are able to identify whether a subject is experiencing mild, moderate, or sever glaucoma, from measuring either the total area, as in FIG. 3C, or the total volume, as in FIG. 4C, where the one-way anova P expression indicates the diagnostic accuracy for the empirical data in these example tests. Diagnostic accuracy can be determined from looking at the superior or inferior areas or volumes. In some examples, the diagnostic accuracy may be different between the two regions. Using the sum of the areas or volumes is also highly accurate for diagnostic purposes.

Figure 7:
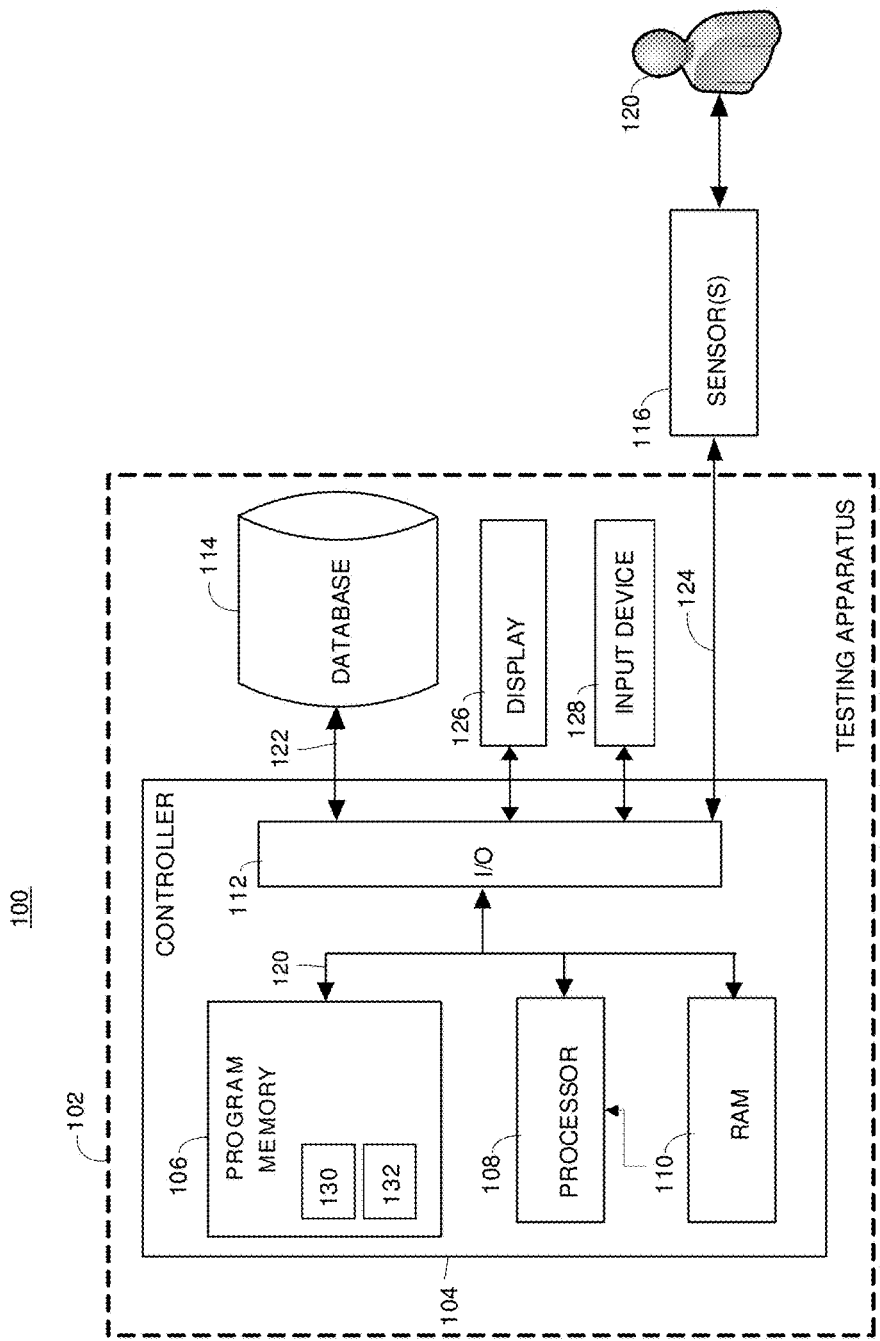
FIG. 7 illustrates an example system for analyzing retinal nerve fiber layers and for detecting glaucoma.

FIG. 7 is an example block diagram 100 illustrating the various components used in implementing an example embodiment of system for analyzing retinal nerve fiber layers and for detecting glaucoma as discussed herein. A glaucoma analysis device 102 may be coupled to a patient 120 via an optical imaging collection (e.g., one optical coherence tomography (OCT) device 116. The processing device 102 may have a controller 104 operatively connected to the database 114 via a link 122 connected to an input/output (I/O) circuit 112. It should be noted that, while not shown, additional databases may be linked to the controller 104 in a known manner. The controller 104 includes a program memory 106, the processor 108 (may be called a microcontroller or a microprocessor), a random-access memory (RAM) 110, and the input/output (I/O) circuit 112, all of which are interconnected via an address/data bus 120. It should be appreciated that although only one microprocessor 108 is shown, the controller 104 may include multiple microprocessors 108. Similarly, the memory of the controller 104 may include multiple RAMs 110 and multiple program memories 106. Although the I/O circuit 112 is shown as a single block, it should be appreciated that the I/O circuit 112 may include a number of different types of I/O circuits. The RAM(s) 110 and the program memories 106 may be implemented as semiconductor memories, magnetically readable memories, and/or optically readable memories, for example. A link 124 may operatively connect the controller 104 to the image collector 116 through the I/O circuit 112. The image collector 116 may be operatively connected to the patient 120.

The program memory 106 and/or the RAM 110 may store various applications (i.e., machine readable instructions) for execution by the microprocessor 108. For example, an operating system 130 may generally control the operation of the testing apparatus 102 and provide a user interface to the analysis device 102 to implement the retinal detection processes 100 described herein. The program memory 106 and/or the RAM 110 may also store a variety of subroutines 132 for accessing specific functions of the testing apparatus 102. By way of example, and without limitation, the subroutines 132 may include, among other things: a subroutine for collecting retinal nerve fiber layer image data from the sensor image collector 116 and other subroutines, for example, implementing software keyboard functionality, interfacing with other hardware in the testing apparatus 102, etc. Other subroutines that may be implemented include: subroutines to segment the neutral nerve fiber layer image data by applying a threshold thickness value; subroutines to determine an area and/or volume of superior retinal nerve thickness data and inferior retinal nerve thickness data; and subroutines to determine the presence or progression of glaucoma in a subject from this volume and/or area superior and/or inferior regions. The program memory 106 and/or the RAM 110 may further store data related to the configuration and/or operation of the analysis device 102, and/or related to the operation of one or more subroutines 152. For example, the image data may be data gathered by the device 116, data determined and/or calculated by the processor 108, etc. In addition to the controller 104, the testing apparatus 102 may include other hardware resources. The analysis device 102 may also include various types of input/output hardware such as a visual display 126 and input device(s) 128 (e.g., keypad, keyboard, etc.). In an embodiment, the display 126 is touch-sensitive, and may cooperate with a software keyboard routine as one of the software routines 132 to accept user input. It may be advantageous for the testing apparatus to communicate with broader medical analysis networks or medical treatment networks (not shown) through any of a number of known networking devices and techniques (e.g., through a commuter network such as a hospital or clinic intranet, the Internet, etc.). For example, the glaucoma analysis device may be connected to a medical records database, hospital management processing system, health care professional terminals (e.g., doctor stations, nurse stations), patient monitoring systems, automated drug delivery systems. Accordingly, the disclosed embodiments may be used as part of an automated closed loop system or as part of a decision assist system.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled,"

however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as examples and does not describe every possible embodiment, as describing every possible embodiment would be impractical, if not impossible. One could implement numerous alternate embodiments, using either current technology or technology developed after the filing date of this application.

What is claimed:

1. A method of analyzing retinal nerve fiber layer for detecting glaucoma and/or other retinal nerve fiber indicated eye conditions in a subject, the method comprising:
   collecting, using a glaucoma analysis processing device, retinal nerve fiber layer image data, the image data containing fiber layer thickness data for a region of interest of the retinal nerve fiber layer image data;
   segmenting, using a glaucoma analysis processing device, the retinal nerve fiber layer image data by removing retinal nerve fiber layer image data below a threshold thickness value over the region of interest, wherein segmenting the retinal nerve fiber layer image data segments a retinal region of interest;
   determining, using a glaucoma analysis processing device and from the segmented retinal nerve fiber layer image data, an area or a volume of the thickness of the retinal nerve fiber layer in the retinal region of interest; and
   determining, using a glaucoma analysis processing device and from the area or the volume, a severity of the glaucoma and/or at least one other of the other retinal nerve fiber indicated eye conditions for the subject.

2. The method of claim 1, wherein the retinal nerve fiber layer image data is optical coherence tomography image data.

3. The method of claim 1, wherein determining the severity of glaucoma and/or at least one other of the other retinal nerve fiber indicated eye conditions for the subject comprises determining the amount of area or volume for the thickness of the retinal nerve fiber layer in the retinal region of interest and comparing that area or volume to a predetermined area or volume indicative of glaucoma and/or at least one other of the other retinal nerve fiber indicated eye conditions.

4. The method of claim 1, wherein determining the severity of glaucoma and/or at least one other of the other retinal nerve fiber indicated eye conditions for the subject comprises determining the amount of area or volume for the thickness of the retinal nerve fiber layer in the retinal region of interest and comparing that area or volume to a previously measured area or volume of the subject.

5. The method of claim 1, wherein determining the severity of glaucoma and/or at least one other of the other retinal nerve fiber indicated eye conditions for the subject comprises determining the amount of area or volume of (i) a superior portion of the retinal nerve fiber layer in the retinal region of interest and/or (ii) an inferior portion of the retinal nerve fiber layer in the retinal region of interest and comparing that area or volume to a predetermined area or volume indicative of glaucoma and/or at least one other of the other retinal nerve fiber indicated eye conditions.

6. The method of claim 1, wherein determining the severity of glaucoma and/or at least one other of the other retinal nerve fiber indicated eye conditions for the subject comprises determining the amount of area or volume of (i) a superior portion of the retinal nerve fiber layer in the retinal region of interest and/or (ii) an inferior portion of the retinal nerve fiber layer in the retinal region of interest and comparing that area or volume to a previously measured area or volume of the subject.

7. The method of claim 1, wherein determining the severity of glaucoma and/or at least one other of the other retinal nerve fiber indicated eye conditions for the subject comprises determining an onset of glaucoma and/or at least one other of the other retinal nerve fiber indicated eye conditions for the subject.

8. The method of claim 1, wherein determining the severity of glaucoma and/or at least one other of the other retinal nerve fiber indicated eye conditions for the subject comprises determining an increase in the severity of glaucoma and/or at least one other of the other retinal nerve fiber indicated eye conditions for the subject.

9. The method of claim 1, wherein the other retinal nerve fiber indicated eye conditions comprise optic neuropathy, toxic/metabolic optic neuropathy, ischanic optic neuropathy, inherited optic neuropathy, multiple sclerosis (MS) with optical neuritis, papilledema, and/or idiopathic intracranial hypertension (IIH).

10. A system comprising:
    one or more processors and one or more memories, the one or more memories storing instructions that when executed by the one or more processors, cause the one or more processors to;
    collect, retinal nerve fiber layer image data, the image data containing fiber layer thickness data for a region of interest of the retinal nerve fiber layer image data;
    segment the retinal nerve fiber layer image data by removing retinal nerve fiber layer image data below a threshold thickness value over the region of interest, wherein segmenting the retinal nerve fiber layer image data segments out a retinal thickness data region of interest;
    determine, from the segmented retinal nerve fiber layer image data, an area or a volume of the desired retinal thickness data region of interest; and
    determine, from the area or the volume, a severity of glaucoma and/or at least one other retinal nerve fiber indicated eye condition for the subject.

11. The system of claim 10, wherein the retinal nerve fiber layer image data is optical coherence tomography image data.

12. The system of claim 10, wherein the one or more memories further store instructions that when executed by the one or more processors, cause the one or more processors to determine the severity of glaucoma and/or the at least one other retinal nerve fiber indicated eye condition for the subject by determining the amount of area or volume for the retinal thickness data region of interest and comparing that area or volume to a predetermined area or volume indicative of glaucoma and/or the at least one other retinal nerve fiber indicated eye condition.

13. The system of claim 10, wherein the one or more memories further store instructions that when executed by the one or more processors, cause the one or more processors to determine the severity of glaucoma and/or the at least one other retinal nerve fiber indicated eye condition for the subject by determining the amount of area or volume for the retinal thickness data region of interest and comparing that area or volume to a previously measured area or volume of the subject.

14. The system of claim 10, wherein the one or more memories further store instructions that when executed by the one or more processors, cause the one or more processors to determine the severity of glaucoma and/or the at least one other retinal nerve fiber indicated eye condition for the subject by determining the amount of area or volume of (i) a superior portion of the retinal thickness data region of interest and/or (ii) an inferior portion of the retinal thickness data region of interest and comparing that area or volume to a predetermined area or volume indicative of glaucoma and/or the at least one other retinal nerve fiber indicated eye condition.

15. The system of claim 10, wherein the one or more memories further store instructions that when executed by the one or more processors, cause the one or more processors to determine the severity of glaucoma and/or the at least one other retinal nerve fiber indicated eye condition for the subject by determining the amount of area or volume of (i) a superior portion of the retinal thickness data region of interest and/or (ii) an inferior portion of the retinal thickness data region of interest and comparing that area or volume to a previously measured area or volume of the subject.

16. The system of claim 10, wherein the one or more memories further store instructions that when executed by the one or more processors, cause the one or more processors to determine the severity of glaucoma and/or the at least one other retinal nerve fiber indicated eye condition for the subject by determining an onset of glaucoma and/or the at least one other retinal nerve fiber indicated eye condition for the subject.

17. The system of claim 10, wherein the one or more memories further store instructions that when executed by the one or more processors, cause the one or more processors to determine the severity of glaucoma and/or the at least one other retinal nerve fiber indicated eye condition for the subject by determining an increase in the severity of glaucoma and/or the at least one other retinal nerve fiber indicated eye condition for the subject.

18. The system of claim 10, wherein the other retinal nerve fiber indicated eye conditions comprise optic neuropathy, toxic/metabolic optic neuropathy, ischanic optic neuropathy, inherited optic neuropathy, multiple sclerosis (MS) with optical neuritis, papilledema, and/or idiopathic intracranial hypertension (IIH).

19. An apparatus for analyzing retinal nerve fiber layers for detecting glaucoma and/or other retinal nerve fiber indicated eye conditions in a subject, the apparatus comprising:
  one or more processors and one or more memories, the one or more memories storing instructions that when executed by the one or more processors, cause the one or more processors to;
  collect, retinal nerve fiber layer image data, the image data containing fiber layer thickness data for a region of interest of the retinal nerve fiber layer image data;
  segment the retinal nerve fiber layer image data by removing retinal nerve fiber layer image data below a threshold thickness value over the region of interest, wherein segmenting the retinal nerve fiber layer image data segments out a superior retinal thickness data region and an inferior retinal thickness data region;
  determine, from the segmented retinal nerve fiber layer image data, an area or a volume of the superior retinal nerve fiber layer thickness data region and the inferior retinal nerve fiber layer thickness data region; and
  a diagnostic module configured to determine, from the area or the volume, a severity of glaucoma and/or at least one other retinal nerve fiber indicated eye condition for the subject.

20. The apparatus of claim 19, wherein the other retinal nerve fiber indicated eye conditions comprise optic neuropathy, toxic/metabolic optic neuropathy, ischanic optic neuropathy, inherited optic neuropathy, multiple sclerosis (MS) with optical neuritis, papilledema, and/or idiopathic intracranial hypertension (IIH).

\* \* \* \* \*

UNITED STATES PATENT AND TRADEMARK OFFICE
CERTIFICATE OF CORRECTION

PATENT NO. : 9,943,223 B2
APPLICATION NO. : 15/041508
DATED : April 17, 2018
INVENTOR(S) : Luis E. Vazquez It is certified that error appears in the above-identified patent and that said Letters Patent is hereby corrected as shown below:

In the Claims

At Column 10, Line 38, "ischanic" should be -- ischemic --.

At Column 10, Line 46, "to;" should be -- to: --.

At Column 12, Line 11, "ischanic" should be -- ischemic --.

At Column 12, Line 22, "to;" should be -- to: --.

At Column 12, Line 42, "ischanic" should be -- ischemic --.

Signed and Sealed this
Twenty-fifth Day of September, 2018

Andrei Iancu
*Director of the United States Patent and Trademark Office*